(12) United States Patent
Zhang

(10) Patent No.: US 9,388,160 B2
(45) Date of Patent: Jul. 12, 2016

(54) QUINAZOLINE DERIVATIVES AS KINASES INHIBITORS AND METHODS OF USE THEREOF

(71) Applicant: TELIGENE LTD., Suzhou (CN)

(72) Inventor: Dawei Zhang, Thousand Oaks, CA (US)

(73) Assignee: Teligene Ltd, Suzhou (CN)

( * ) Notice: Subject to any disclaimer, the term of this patent is extended or adjusted under 35 U.S.C. 154(b) by 13 days.

(21) Appl. No.: 14/351,557

(22) PCT Filed: Oct. 12, 2012

(86) PCT No.: PCT/CN2012/001371
§ 371 (c)(1),
(2) Date: Apr. 11, 2014

(87) PCT Pub. No.: WO2013/053206
PCT Pub. Date: Apr. 18, 2013

(65) Prior Publication Data
US 2014/0235658 A1    Aug. 21, 2014

Related U.S. Application Data

(60) Provisional application No. 61/627,359, filed on Oct. 12, 2011.

(51) Int. Cl.
| | | |
|---|---|---|
| *C07D 401/04* | (2006.01) |
| *C07D 405/14* | (2006.01) |
| *A61K 31/517* | (2006.01) |
| *A61K 31/5377* | (2006.01) |
| *A61K 31/55* | (2006.01) |
| *A61K 31/551* | (2006.01) |
| *A61K 31/553* | (2006.01) |
| *C07D 405/12* | (2006.01) |
| *C07D 239/94* | (2006.01) |
| *A61K 45/06* | (2006.01) |

(52) U.S. Cl.
CPC ............ *C07D 401/04* (2013.01); *A61K 31/517* (2013.01); *A61K 31/5377* (2013.01); *A61K 31/55* (2013.01); *A61K 31/551* (2013.01); *A61K 31/553* (2013.01); *A61K 45/06* (2013.01); *C07D 239/94* (2013.01); *C07D 405/12* (2013.01); *C07D 405/14* (2013.01)

(58) Field of Classification Search
CPC ... A01N 43/54; A61K 31/517; C07D 239/72; C07D 401/00
USPC ................................ 514/266.2; 544/283, 284
See application file for complete search history.

(56) References Cited

U.S. PATENT DOCUMENTS

| | | | |
|---|---|---|---|
| 7,223,749 B2 | 5/2007 | Himmelsbach et al. | |
| 7,863,281 B2 | 1/2011 | Himmelsbach et al. | |
| 2004/0044014 A1* | 3/2004 | Himmelsbach et al. | ... 514/266.4 |
| 2004/0158065 A1 | 8/2004 | Barth | |
| 2005/0107358 A1* | 5/2005 | Himmelsbach et al. | . 514/211.15 |
| 2005/0159436 A1 | 7/2005 | Himmelsbach et al. | |
| 2006/0178634 A1* | 8/2006 | Wyrick | ......................... 604/157 |
| 2007/0037781 A1* | 2/2007 | Konetzki et al. | .............. 514/171 |
| 2007/0185081 A1 | 8/2007 | Himmelsbach et al. | |
| 2008/0103161 A1 | 5/2008 | Himmelsbach | |

FOREIGN PATENT DOCUMENTS

| | | |
|---|---|---|
| EP | WO03089439 A1 | 10/2003 |
| EP | WO2004074263 A1 | 9/2004 |
| WO | WO2004069791 A2 | 8/2004 |

* cited by examiner

*Primary Examiner* — Paul V Ward
(74) *Attorney, Agent, or Firm* — Feng Tian

(57) ABSTRACT

The present invention is directed to novel quinazolines, their derivatives, pharmaceutically acceptable salts, solvates, prodrug, stereoisomer, tautomer, metabolite and hydrates thereof. The compounds and compositions of the present invention have protein kinases inhibitory activities and are expected to be useful for the treatment of protein kinases mediated diseases and conditions.

4 Claims, No Drawings

QUINAZOLINE DERIVATIVES AS KINASES INHIBITORS AND METHODS OF USE THEREOF

CROSS REFERENCE

The application is a 35 U.S.C. §371 national stage filing of International Patent Application PCT/CN2012/001371 (published as WO 2013/053206 A1), filed Oct. 12, 2012, which is entitled to priority pursuant to 35 U.S.C. §119(e) to U.S. Provisional Application No. 61/627,359, filed Oct. 12, 2011. The entire disclosures of the afore-mentioned patents are hereby incorporated by reference in their entirety.

FIELD OF THE INVENTION

The present invention is directed to inhibitors of kinase and pharmaceutically acceptable salts, solvates, hydrates, prodrugs and metabolites thereof, the preparation method thereof, and the use of such compounds to treat kinase mediated diseases and conditions such as cancer.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. For example, protein tyrosine kinases (PTKs) are enzymes, which catalyze the phosphorylation of specific tyrosine residues in cellular proteins. Examples of kinases in the protein kinase family include, without limitation, Abl1 (v-Abl Abelson murine leukemia viral oncogene homolog 1), Akt, Alk, Bcr-Abl1, Blk, Brk, Btk, c-Kit, c-Met, c-Src, c-Fms, CDK1-10, b-Raf, c-Raf1, CSF1R, CSK, EGFR, ErbB2, ErbB3, ErbB4, Erk, FGFR1, FGFR2, FGFR3, FGFR4, FGFR5, Flt-1, Fps, Frk, Jak, KDR, MEK, PDGFR, PIK, PKC, PYK2, Ros, Tie, Tie2, and Zap70. Due to their activity in numerous cellular processes, protein kinases have emerged as important therapeutic targets.

Epidermal growth factor (EGF) is a widely distributed growth factor that in cancer, can stimulate cancer-cell proliferation, block apoptosis, activate invasion and metastasis, and stimulate angiogenesis (Citri, et al., *Nat. Rev. Mol. Cell. Biol.* 7:505, 2006; Hynes, et al., *Nat. Rev. Cancer* 5:341, 2005). The EGF receptor (EGFR or ErbB) is a transmembrane, tyrosine kinase receptor that belongs to a family of four related receptors. The majority of human epithelial cancers are marked by functional activation of growth factors and receptors of this family (Ciardiello, et al., *New Eng. J. Med.* 358: 1160, 2008) so that EGF and EGFR are natural targets for cancer therapy. The human epidermal growth factor receptor (HER) tyrosine kinase family consists of four structurally related cellular receptors: the epidermal growth factor receptor (EGFR; HER1), HER2 (ErbB2), HER3 (ErbB3), and HER4.

Quinazolines are a known class of kinase inhibitors with utility for the treatment of cancer, angiogenesis disorders, and inflammatory disorders. To this end, attempts have been made to identify small molecules which act as protein kinase inhibitors. For example, quinazoline derivatives (PCT WO 00177104; U.S.20050250761; WO2004069791) have been described as HER kinase inhibitors. EGFR inhibitors Erlotinib and Gefitinib as well as the dual EGFR/HER2 inhibitor Lapatinib are FDA-approved cancer drugs that are effective against multiple solid tumor cancers. However, their effectiveness is also limited by the drug resistance that frequent emerges following treatment.

Thus, the compounds that can inhibit protein kinases such as HER kinases activity with improved efficacy or overcoming drug resistance are highly desired.

SUMMARY OF THE INVENTION

The present invention provides compounds of Formula I:

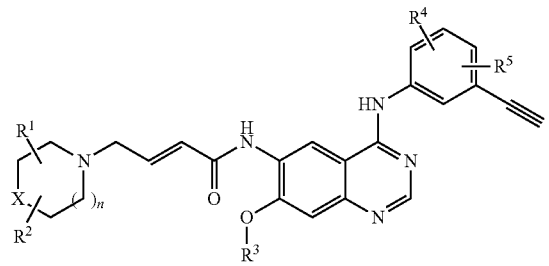

I or a pharmaceutically acceptable salt, solvate or a prodrug or a stereoisomer or a tautomer or metabolite thereof, wherein
$R^1$ and $R^2$ are independently selected from hydrogen, $C_1$-$C_3$ alkyl, and F;
$R^3$ is selected from
$C_1$-$C_6$ straight or branched alkyl, optionally substituted by one or more halogens or $C_1$-$C_3$ alkoxy group;
tetrahydrofuran-3-yl;
—$(CH_2)_m$-morpholine, and —$(CH_2)_m$-piperazine-N($C_1$-$C_3$ alkyl);
m is 2 or 3;
n is 0, 1, 2 or 3;
X is selected from
carbon with n is an integer from 0 to 3, inclusive; and
O or N—$R^6$ with n is an integer from 1 to 2, inclusive;
$R^4$ and $R^5$ are independently selected from hydrogen, $C_1$-$C_3$ alkyl, F, and Cl;
$R^6$ is $C_1$-$C_3$ alkyl, optionally substituted by one or more halogens, hydroxyl or $C_1$-$C_3$ alkoxy group.

The present invention further provides pharmaceutical compositions comprising a compound of formula I described above and a pharmaceutically acceptable carrier.

The present invention further provides methods for regulating the kinase signaling transduction comprising administrating to a mammalian subject a therapeutically effective amount of any of the compounds of formula I described above.

DETAILED DESCRIPTION OF THE INVENTION

In some embodiments of the present invention, there are provided compounds of Formula I:

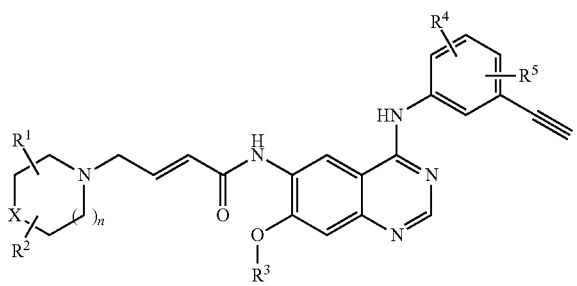

or a pharmaceutically acceptable salt, solvate or a prodrug or a stereoisomer or a tautomer or metabolite thereof, wherein $R^1$ and $R^2$ are independently selected from hydrogen, $C_1$-$C_3$ alkyl, and F;

$R^3$ is selected from $C_1$-$C_6$ straight or branched alkyl, optionally substituted by one or more halogens or $C_1$-$C_3$ alkoxy group;

tetrahydrofuran-3-yl;

—$(CH_2)_m$-morpholine, and —$(CH_2)_m$-piperazine-N($C_1$-$C_3$ alkyl);

m is 2 or 3;

n is 0, 1, 2 or 3;

X is selected from carbon with n is an integer from 0 to 3, inclusive; and

O or N—$R^6$ with n is an integer from 1 to 2, inclusive;

$R^4$ and $R^5$ are independently selected from hydrogen, $C_1$-$C_3$ alkyl, F, and Cl;

$R^6$ is $C_1$-$C_3$ alkyl, optionally substituted by one or more halogens, hydroxyl or $C_1$-$C_3$ alkoxy group.

In some preferred embodiments, herein provide compounds of Formula II:

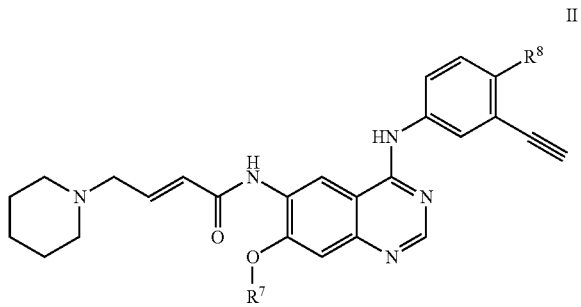

or a pharmaceutically acceptable salt, solvate or a prodrug or a stereoisomer or a tautomer or metabolite thereof, wherein $R^7$ is selected from $C_1$-$C_3$ straight or branched alkyl, optionally substituted by one or more halogens or $C_1$-$C_3$ alkoxy group, and tetrahydrofuran-3-yl; and $R^8$ is H or F.

In certain embodiments, $R^1$ or $R^2$ is a hydrogen. In other embodiments, both $R^1$ and $R^2$ are hydrogen. In other embodiments, $R^1$ is F. In some embodiments, $R^3$ is a methyl. In other embodiments $R^3$ is an ethyl. In certain embodiments, $R^3$ is tetrahydrofuran-3-yl. In other embodiments, $R^4$ or $R^5$ is a hydrogen. In some embodiments, $R^7$ is an methyl or ethyl. In certain embodiments, $R^8$ is a hydrogen. In another embodiments, n is 1. In certain embodiments, m is 2. In some embodiments, X is a carbon. In other embodiments, the compound of Formula I-II is in the form of pharmaceutically acceptable salt. In some embodiments, the compound of Formula I-II is in the form of a solvate. In other embodiments, the compound of Formula I-II is in the form of a metabolite. In other embodiments, the compound of Formula I-II is in the form of a prodrug. In some embodiments, the compound of Formula I-II is a stereoisomer. In other embodiments, the compound of Formula I-II is a tautomer. In another embodiment, the deuterium enrichment in compounds of Formula I-II is at least about 1%.

In certain embodiments, there are provided compounds without limitation selected from the group consisting of:

(E)-N-(4-((3-ethynylphenyl)amino)-7-methoxyquinazolin-6-yl)-4-(piperidin-1-yl)but-2-enamide;

(E)-N-(7-ethoxy-4-((3-ethynylphenyl)amino)quinazolin-6-yl)-4-(piperidin-1-yl)but-2-enamide;

(E)-N-(4-((3-ethynylphenyl)amino)-7-(2-fluoroethoxy)quinazolin-6-yl)-4-(piperidin-1-yl)but-2-enamide;

(E)-N-(4-((3-ethynyl-4-fluorophenyl)amino)-7-methoxyquinazolin-6-yl)-4-(piperidin-1-yl)but-2-enamide;

(E)-N-(4-((3-ethynylphenyl)amino)-7-((tetrahydrofuran-3-yl)oxy)quinazolin-6-yl)-4-(piperidin-1-yl)but-2-enamide;

(E)-N-(4-((3-ethynylphenyl)amino)-7-(2-methoxyethoxy)quinazolin-6-yl)-4-(piperidin-1-yl)but-2-enamide;

(E)-N-(4-((3-ethynylphenyl)amino)-7-$d_3$-methoxyquinazolin-6-yl)-4-(piperidin-1-yl)but-2-enamide; and (E)-N-(7-$d_5$-ethoxy-4-((3-ethynylphenyl)amino)quinazolin-6-yl)-4-(piperidin-1-yl)but-2-enamide;

and the like, or a pharmaceutically acceptable salt, solvate, or a prodrug, or a metabolite thereof.

In some embodiments, the present invention provides pharmaceutical compositions comprising a compound of formula I-II and a pharmaceutically acceptable carrier. In certain embodiments, the compositions are for the treatment of a disease regulated by a protein kinase. In certain embodiments, the compositions are for or the treatment of a hyperproliferative disorder. In other embodiments, the pharmaceutical compositions are suitable for oral, parenteral, or intravenous administration.

In some embodiments, the compound(s) of Formula I-II are used to treat a subject by administering the compound(s) as a pharmaceutical composition. To this end, the compound(s), in one embodiment, are combined with one or more pharmaceutically acceptable excipients, including carriers, diluents or adjuvants, to form a suitable composition, which is described in more detail herein.

In some embodiments, the present invention provides methods for regulating the kinase signaling transduction comprising administrating to a mammalian subject a therapeutically effective amount of a compound of Formulas I-II.

In other embodiments provide herein methods for treating or preventing a HER Kinases (including all mutant kinases) mediated disorder, said method comprises administrating to a mammalian subject a therapeutically effective amount of a compound of Formula I-II.

In yet another aspect, there are provided herein methods for inhibiting EGFR kinases, said method comprises administrating to a mammalian subject a therapeutically effective amount of a compound of Formulas I-II.

In other embodiments provide herein methods for treating neoplasia comprising administrating to a mammalian subject in need thereof, a therapeutically effective amount of a compound of Formulas I. In certain embodiments, the neoplasia is selected from breast cancer, pancreatic carcinoma, non-small cell lung cancer, non-hodgkin's lymphoma, colorectal cancer, and prostate cancer. In certain embodiments, the neoplasia is lung cancer. In some embodiments, the methods further comprise administering one or more anti-cancer agents.

In other embodiments, there are provided methods for treating or preventing a hyper-proliferative comprising administrating to a mammalian subject a therapeutically effective amount of a compound of Formulas I-II.

The following definitions should assist in understanding the invention described herein.

The term "alkyl" is intended to include linear, branched, cyclic hydrocarbon group, which may be unsubstituted or optionally substituted with one or more functional groups. $C_1$-$C_3$ alkyl is intended to include $C_1$, $C_2$ and $C_3$ alkyl groups. $C_1$-$C_6$ alkyl is intended to include $C_1$, $C_2$, $C_3$, $C_4$, $C_5$ and $C_6$ alkyl groups. Examples of alkyl include, but not limited to, methyl, ethyl, n-propyl, isopropyl, cyclopropyl, etc. Alkyl may be substituted or unsubstituted. Illustrative substituted alkyl group include, but are not limited to, fluoromethyl, difluoromethyl, trifluoromethyl, hydoxymethyl, methoxymethyl, 2-fluoroethyl, 2-methoxyethyl, etc.

Halogen means fluorine, chlorine, bromine, and iodine.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as Deterium and carbon such as $^{13}C$. Deuterium (D or $^2H$) is a non-radioactive, stable isotope of hydrogen, the natural abundance of deuterium is 0.015%. Compound should be considered to be unnatural, if its level of deuterium has been enriched to be greater than their natural abundance level 0.015%. In a compound of this invention, it is understood that the abundance of deuterium is substantially greater than the natural abundance of deuterium, which is 0.015%, when a particular position is designated as deuterium. The concentration of naturally abundant stable hydrogen is small and immaterial compared to the degree of stable isotopic substitution of compounds of this invention.

The term "comprising" is meant to be open-ended, including the indicated component(s), but not excluding other elements.

The term "pharmaceutically acceptable" when used with reference to a compound of Formulas I or II is intended to refer to a form of the compound that is safe for administration to a subject. For example, a free base, a salt form, a solvate, a hydrate, a prodrug or derivative form of a compound of Formula I or II, which has been approved for mammalian use, via oral ingestion or any other route of administration, by a governing authority or regulatory agency, such as the Food and Drug Administration (FDA) of the United States, is pharmaceutically acceptable.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

In synthesizing a compound of formulas I-II according to a desired procedure, the steps in some embodiment, are performed in an order suitable to prepare the compound, including a procedure described herein or by an alternate order of steps described herein, and in one embodiment, be preceded, or followed, by additional protection/deprotection steps as necessary. In certain embodiment, the procedures are further use appropriate reaction conditions, including inert solvents, additional reagents, such as bases (e.g., LDA, DIEA, pyridine, $K_2CO_3$, and the like), catalysts, and salt forms of the above. The intermediates in some embodiments are isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of this invention in some embodiments also are represented in multiple tautomeric forms. The invention expressly includes all tautomeric forms of the compounds described herein.

The compounds in one embodiment also occur in cis- or trans- or E- or Z-double bond isomeric forms. All such isomeric forms of such compounds are expressly included in the present invention.

INDICATION

The present invention provides compounds which are capable of modulating one or more signal transduction pathways comprising, but not limited to EGFR kinase.

By the term "modulating," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present invention can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymphangiogenesis (lymphatic vessel growth), and/or hematopoiesis (e.g., T- and B-cell development, dendritic cell development, etc.).

While not wishing to be bound by any theory or mechanism of action, it has been found that compounds of the present invention possess the ability to modulate kinase activity. The methods of the present invention, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

FORMULATIONS AND METHOD OF USE

The amount of compound(s) which is/are administered and the dosage regimen for treating cancer with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg, and even more advantageously between about 0.25 and about 1 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients.

Routes of Adminstration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nanoparticulates, gels, solid solution, liposome, films (including muco-adhesive), ovules, sprays and liquid formulations.

Biological Assays:

As stated hereinbefore, the compounds defined in the present invention possess biological activity. These properties may be assessed, for example, using one or more of the procedures set out below:

(a) An in vitro assay which determines the ability of a test compound to inhibit EGFR kinase activity.
 1. Materials: EGFR (BPS#40187, Lot#80925, 25 ng/Reaction); Poly (Glu, Tyr) sodium salt, (4:1, Glu:Tyr) (Sigma#P7244) Kinase-Glo Plus Luminescence; kinase assay kit (Promega#V3772); Substrates, 0.2 mg/ml poly (Glu, Tyr); ATP, 10 µM; Compounds test range, 0.1 nM-3 µM.
 2. The assay was performed using Kinase-Glo Plus luminescence kinase assay kit (Promega). It measures kinase activity by quantitating the amount of ATP remaining in solution following a kinase reaction. The luminescent signal from the assay is correlated with the amount of ATP present and is inversely correlated with the amount of kinase activity. The compounds were diluted in 10% DMSO and 5 µl of the dilution was added to a 50 µl reaction so that the final concentration of DMSO is 1% in all of reactions. All of the enzymatic reactions were conducted at 30° C. for 25 minutes. The 50 µl reaction mixture contains 40 mM Tris, pH 7.4, 10 mM $MgCl_2$, 0.1 mg/ml BSA, 1 mM DTT, 0.2 mg/ml Poly (Glu, Tyr) substrate, 10 µM ATP and EGFR (Table 2.3.1). After the enzymatic reaction, 50 µl of Kinase-Glo Plus Luminescence kinase assay solution (Promega) was added to each reaction and incubate the plate for 5 minutes at room temperature. Luminescence signal was measured using a BioTek Synergy 2 microplate reader.
 3. EGFR activity assays were performed in duplicate at each concentration. The luminescence data were analyzed using the computer software, Graphpad Prism. The difference between luminescence intensities in the absence of EGFR ($Lu_t$) and in the presence of EGFR ($Lu_c$) was defined as 100% activity ($Lu_t$-$Lu_c$). Using luminescence signal (Lu) in the presence of the compound, % activity was calculated as: % activity={($Lu_t$-Lu)/($Lu_t$-$Lu_c$)}×100%, where Lu=the luminescence intensity in the presence of the compound (all percent activities below zero were shown zero in the table). The values of % activity versus a series of compound concentrations were then plotted using non-linear regression analysis of Sigmoidal dose-response curve generated with the equation $Y=B+(T-B)/1+10^{(LogEC50-X) \times Hill\ Slope)}$, where Y=percent activity, B=minimum percent activity, T=maximum percent activity, X=logarithm of compound and Hill Slope=slope factor or Hill coefficient. The IC50 value was determined by the concentration causing a half-maximal percent activity.

(b) An in vitro assay which determines the ability of a test compound to inhibit EGFR(T790M/L858R) kinase activity.

The assay was performed under a similar condition to the one that has been described above for (a) An in vitro assay which determines the ability of a test compound to inhibit EGFR kinase activity, except that the following enzyme EGFR(T790M/L858R) (BPS#40350, Lot#101214) was used.

The following Table A lists compounds representative of the invention and their activity in EGFR and EGFR(T790M/L858R) assays.

TABLE A

| Compound | EGFR $IC_{50}$ | EGFR(T790M/L858R) $IC_{50}$ |
|---|---|---|
| 11 | 1.7 nM | 22 nM |
| 12 | <10 nM | <100 nM |

A representative number of compounds were assayed against different cancer cell lines such as NCI-H-1975 or A431 using the cell proliferation assays:

Cell Proliferation Assays:
1. $5 \times 10^3$ cells per well in 100 µl of medium were seeded in 96-well plate, here the medium contained 5% FBS
2. 24 hours later, 100 µl fresh medium was added with various concentrations of compounds into each well, while the medium here was free of FBS
3. After the cells were treated with compounds for 72 hours, 20 µl MTT (5 mg/ml) was added into each well, and then the assay plate was incubated at 37° C. for 4 more hours.
4. The assay plate was centrifuged at 800 g for 10 min. The medium was aspirated, 150 µl DMSO was added into each well. The plate was gently shaked for 10 min.
5. The absorbance at 570 nm was measured on the plate reader.
6. IR %=(WC−WT)/WC*100%.

The following Table B lists compounds representative of the invention and their activity in Cell assays.

TABLE B

| Compound | SK-Br-3 Cell line $IC_{50}$ | A431 Cell line $IC_{50}$ |
|---|---|---|
| 11 | 85.23 nM | 2.95 µM |
| 12 | 115.6 nM | 4.90 µM |
| Dacomitinib | 224.6 nM | 19.48 µM |

A representative number of compounds were tested in Ames Assay for assess the mutagenic potential.

Ames Assay:
Preparations of culture media/plates and reagents: 0.5 mmol L-histidine-0.5 mmol/L biotin solution; 20% glucose solution; nutrient broth; KCl salt solution (1.65 M KCl+0.4 M $MgCl_2$); 0.2 M phosphate buffer (pH 7.4); co-factors (NADP; glucose 6-phosphate) for S9 mixture; top agar medium; minimal agar medium (Vogel-Bonner medium E); bottom agar medium.

Preparation of the enriched culture: Take nutrient broth 5 mL, added it to sterile tubes with the cryopreserved strain culture TA1535 and TA1537. After inoculation in nutrient broth, the cultures were kept at 37° C. with oscillation of 100 times/min for 10 hours. The strain cultures should have about $1~2 \times 10^9$ viable cells per milliliters.

Preparation of 10 ml S9 mixture: Co-factor mixture 9 mL by glucose 6-phosphate 42.3 mg, NADH 14.2 mg, 6-phosphate dehydrogenase (3 unit/µl) 10 µl plus riboflavin (9.6 mg dissolved in 700 µL water), and then mixed with 1 ml of the induced rat S9.

Plate incorporation method: In the experiment, place 2 ml of the top agar medium containing 0.5 mmol/L histidine-0.5 mmol/L biotin into the test tubes kept in 45° C. water bath. Into a 1.5 ml sterile Eppendorf tube, it was added 0.1 ml of the bacterial strain in the enriched broth, 0.1 ml of the test compound solution and 0.5 ml of the S9 mixture, thoroughly mixed and incubated for 30 minutes at 37° C. with shaker speed at 150 rpm/min. The liquid mixture in the Eppendorf tube was added to the top agar medium. After mixing it was poured rapidly into the plates with bottom agar plate, turning the plates to allow uniform distribution. Initially placed horizontally for condensation and then placed invertly for 48 hours at 37° C. Count and record the number of revertant colonies per dish.

Experiment controls: In addition to the set of doses (3.3, 8.3, 33.3 and 66.6 µM) for the test compounds, here are the controls: blank control, sterile control, solvent control, positive mutagen control (2-aminoanthracene at 10 µg/dish).

The following Table C lists compounds representative of the invention and their activity in Ames Assay.

TABLE C

| Compound | Concentration uM | TA1535 Colony number | TA1537 Colony number |
|---|---|---|---|
| Control Spontaneous mutation | | 19 | 7 |
| 2-aminoanthracene at 10 µg/dish | 17.27 | 205 | 260 |
| 11 | 66.6 | 12 | 22 |
|  | 33.3 | 18 | 23 |
|  | 8.33 | 13 | 12 |
|  | 3.33 | 10 | 14 |
| 12 | 66.6 | 9 | 66 |
|  | 33.3 | 17 | 47 |
|  | 8.33 | 9 | 22 |
|  | 3.33 | 17 | 8 |

Compound 11 was negative, and compound 12 was positive in Ames Assay.

In Vivo Xenograft Assay:
A representative protocol for the in vivo experiment is as followed to establish the subcutaneous NCI-H-1975 cell line xenograft model in nude mice and to evaluate the in vivo therapeutic efficacy of the compounds: Animals: Male Balb/c nude mice (6~8 weeks old) were obtained from SLAC Laboratory Animal, Shanghai, China. Animals were maintained under SPF conditions in sterile filter top cages and housed on HEPA-filtered ventilated racks. Animals received sterile rodent chow and water ad libitum. Cell line: NCI-H-1975 cell line, S.c. Xenograft Models in Athymic Mice: Cells for implantation into athymic mice were harvested and pelleted by centrifugation at 1200 r/min for 5 min. Cells were washed once and resuspended in sterile PBS buffer with $5 \times 10^6$ in 200 µl. Then cells were implanted s.c. into the right scapular region of each mouse and allowed to grow to 200-300 $mm^3$ before the administration of compound. Preparation of the Dose Formulation: each compound was suspensioned in 0.5% CMC-Na. Randomization: When tumor volumes approach 200-300 $mm^3$, the mice will be randomized into 5 groups according to the tumor volume. The day will be denoted as D1 and the treatments will be started at this day. Administered: Dose will be administered with oral gavage needle once daily for number of days. Treatment of compounds administered in 0.5% CMC—Na by p.o. gavage was initiated when tumors were 200~300 $mm^3$ in volume. Observations: After inoculation, the animals will be checked daily for morbidity and mortality. At the time of routine monitoring, the animals will be checked for any effects of tumor growth and treatments on normal behavior such as mobility, body weight gain/loss (body weights will be measured twice weekly or every other day), eye/hair matting and any other abnormal effect. Death and observed clinical signs will be recorded on the basis of the numbers of animals within each subset. Tumor Size Measurements: Tumor volume was determined by measurement with electronic vernier calipers every 3 days and tumor volume was calculated as the product of its length×$width^2$×0.5. Effect studies: Tumor volume was expressed on indicated days as the mean tumor volume±SD. Percentage (%) inhibition values were measured for drug-treated mice compared with vehicle-treated mice and are calculated as follows: Tumor growth inhibition(TGI, %)=100−[MTV treated/MTV control]×100. Significant differences between the treated versus the control groups (p<0.05) were determined using t test. At study endpoint, after blood collection, mice were practicsed euthanasia by cervical dislocation, the tumor tissue was collected first, then abdominal cavity was cut open, liver and spleen were excised, then weight after the gallblader was removed respectively. Organ weight and Organ/body weight ratios between the treated versus the control groups were compared. Ratios was calculated as follows: Ratios=Organ weight/(body weight-tumor weight). Both organ weight and Organ/body weight ratios were also expressed as mean±SD, and significant differences between the treated versus the control groups (p<0.05) were determined using t test.

The following Table D lists compounds representative of the invention and their activity in subcutaneous NCI-H-1975 cell line xenograft model in nude mice described above. Compound 11 and Dacomitinib were dosed at 15 mg/kg by oral gavage once daily for number of days. Tumor growth inhibition (TGI, %) was calculated. Compound 11 showed significant better tumor growth inhibition compared with Dacomitinib.

TABLE D

Tumor growth inhibition (TGI, %)

| | Compound | |
| Days | 11 | Dacomitinib |
| --- | --- | --- |
| 3 | 30.11% | 19.86% |
| 7 | 83.25% | 75.36% |

SYNTHEIS OF COMPOUNDS

The compounds of Formulas I-II can be synthesized according to the procedures described in the following Schemes to those skilled in the art, wherein the substituents are as defined for Formulas I-II above, except where further noted. The synthetic methods described below are merely exemplary, and the compounds of the invention may also be synthesized by alternate routes as appreciated by persons of ordinary skill in the art.

The synthesis of compound 7 can be conducted by reaction as described in Scheme 1. A few synthetic methods that can lead to the preparation of compounds of Formulas I-II have been reported in the literature (U.S.20050250761, U.S. application Ser. No. 07/019,012, or U.S.20100240649).

The reaction of commercial available starting materials 1 and 2 in alcohol such as isopropyl alcohol can lead to the synthesis of compound 3. The replacement of fluoride in 3 with salt $R^3ONa$ in a solution of $R^3OH$ with heat will give compound 4 ($R^3$ has been previously defined in the invention). The nitro group can be selectively reduced to the amino group with metal such as Fe, Zinc or $SnCl_2$ etc to generate compound 5. (Tetrahedron, 64(44), 10195-10200, 2008; Tetrahedron Letters, 42(46), 8141-8142; 2001; Faming Zhuanli Shenqing Gongkai Shuomingshu, 1313274, 19 Sep. 2001). The synthesis of compound 6 has been reported in the literature and reaction of compound 5 and 6 in solvent such as DMAC will afford the desired product 7.

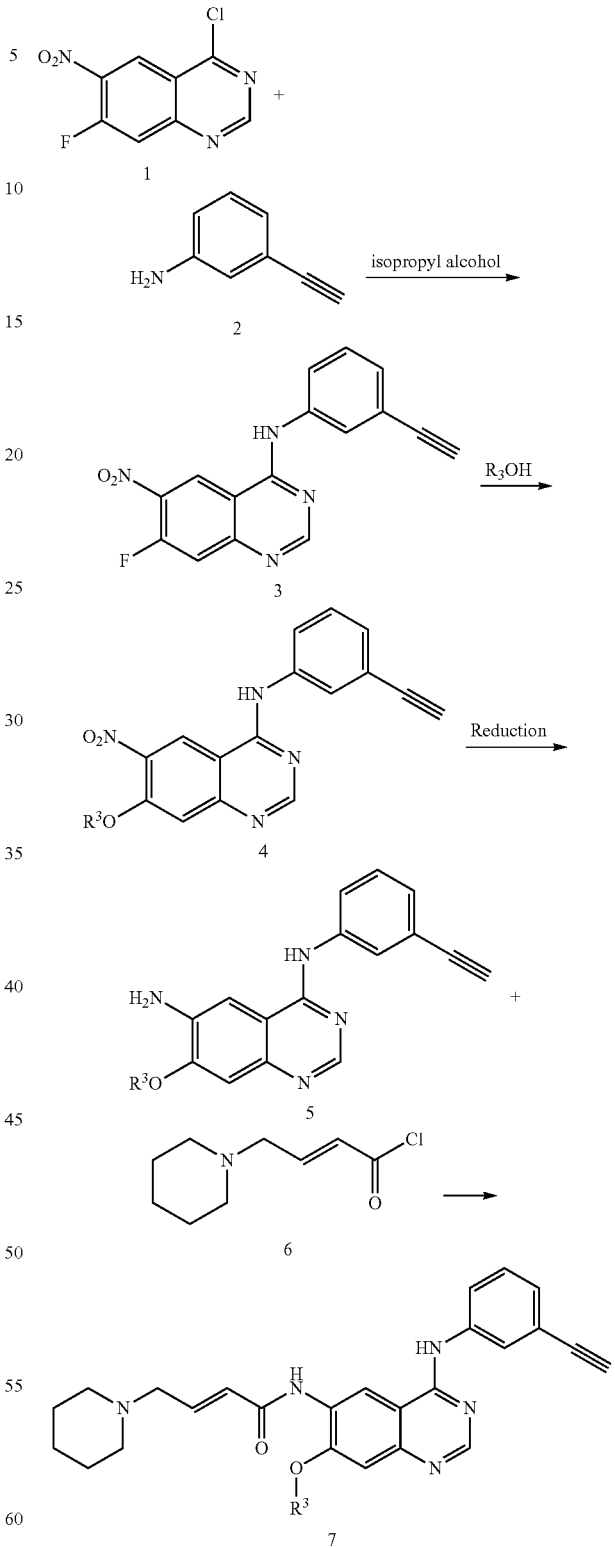

Scheme 1

The synthesis of compound 11 is described in Scheme 2. Compound 1 was dissolved in dichloromethane, and a solution of compound 2 in isopropanol was added. The resulting mixture was stirred at room temperature for 15 minutes when a precipitate of product formed. After 15 minutes hexane was added to ensure complete precipitation, and the solid was collected by filtration and dissolved in aqueous MeOH. Neutralization with $Et_3N$ and further dilution with water gave compound 3. NaH was added in potions to ethanol, the reaction is stirred at room temperature for 1 hour then was added compound 3. The reaction mixture is first heated at 65° C. for overnight, then cool to room temperature followed by quenching with water. The solvent is removed under vacuum then the solid can be filtered to afford compound 8. A solution of compound 8 in ethanol, water and glacial acetic acid is heated for reflux and iron was added in batches. The reaction was refluxed for another 4 hours and cooled to room temperature. Work up and chromatography using $CH_2Cl_2$ and methanol to give the compound 9. To a solution of compound 10 in dichloromethane is added oxalyl chloride and several drops of DMF. The reaction is stirred at room temperature for 1-2 hours and all the solvent is removed. The resulting residue was dissolved in THF and cooled to 0° C. A mixture of compound 9 and triethyl amine was added. The reaction is stirred at 0° C. for 1-2 hours, water is added and all the solvent is removed under vacuum. The product is extracted with dichloromethane, dried over with $MgSO_4$, filtered and concentrated. Purification by chromatography afforded compound 11.

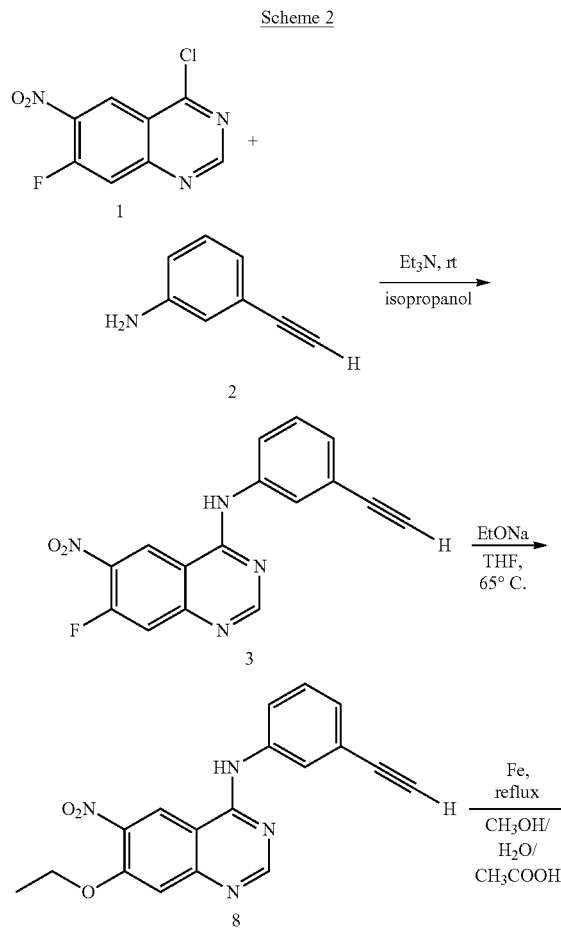

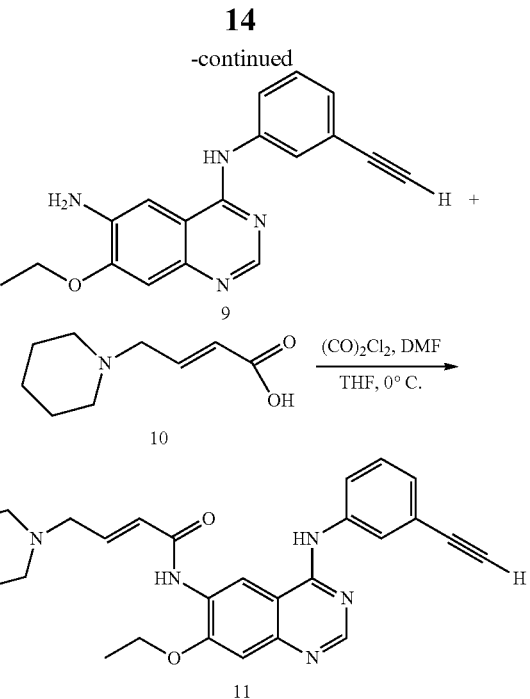

DESCRIPTION OF EMBODIMENTS

These detailed descriptions are presented for illustrative purposes only and are not intended as a restriction on the scope of the invention.

Proton NMR Spectra

Unless otherwise indicated, all $^1H$ NMR spectra were run on a Varian series Mercury 300, 400 and 500 MHz instrument or a Bruker series 300, 400 and 500 MHz instrument. Where so characterized, all observed protons are reported as parts-per-million (ppm) downfield from tetramethylsilane (TMS) or other internal reference in the appropriate solvent indicated.

ABBREVIATION

DMF means N,N-dimethylformamide.
DCM means dichloromethane
DIPEA means diisopropyl ethylamine.
EA means ethylamine.

EXAMPLE 1

The Synthesis of (E)-N-(7-ethoxy-4-((3-ethynylphenyl)amino)quinazolin-6-yl)-4-(piperidin-1-yl)but-2-enamide (Compound 11)

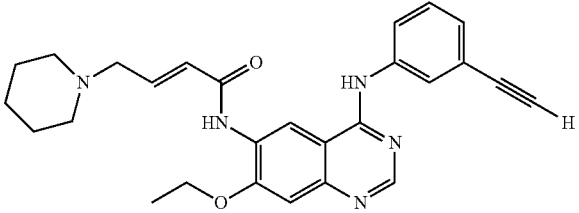 [SMILES: C#Cc1cccc(Nc2ncnc3cc(OCC)c(NC(=O)/C=C/CN4CCCCC4)cc23)c1]

Step 1: the Synthesis of 4-chloro-7-fluoro-6-nitroquinazoline (Compound 1)

7-fluoro-6-nitroquinazolin-4-ol (15 g, 0.072 mol) was added to 150 ml SOCl$_2$ and 10 drops of DMF was added. The solution was heated to reflux for 4 hours which become a clear solution, then the SOCl$_2$ was removed under reduce pressure to give 4-chloro-7-fluoro-6-nitroquinazoline as yellow powder 15.4 g (94.4% yield).

Step 2: the Synthesis of N-(3-ethynylphenyl)-7-fluoro-6-nitroquinazolin-4-amine (Compound 3)

4-chloro-7-fluoro-6-nitroquinazoline (12 g, 0.052 mol) was dissolved in 120 ml DCM. A solution of 3-ethynylaniline (7 g, 0.057 mol) in 200 ml isopropanol was added dropwise in an ice bath. The solution was stirred for 1 hour in the ice bath, then TEA (7 g, 0.069 mol) was added and allowed to stir for another 0.5 hour at room temperature. Yellow precipitate was formed and the solid was filtered and washed with 20 ml isopropanol twice, dried to give N-(3-ethynylphenyl)-7-fluoro-6-nitroquinazolin-4-amine 8.2 g as a yellow solid (50.3% yield).

Step 3: the Synthesis of 7-ethoxy-N-(3-ethynylphenyl)-6-nitroquinazolin-4-amine (Compound 8)

Na (1.4 g, 0.060 mol) was carefully dissolved in 80 ml of anhydrous ethanol to form a clear solution, then N-(3-ethynylphenyl)-7-fluoro-6-nitroquinazolin-4-amine (8 g, 0.025 mol) was added and stirred for 4 hours at 80° C. The solution was concentrated under reduced pressure to remove excess ethanol, and 50 ml H$_2$O was added. The resulting solid precipitate was filtered and dried under vacuum to get 7-ethoxy-N-(3-ethynylphenyl)-6-nitroquinazolin-4-amine as yellow solid 8.1 g (93.4% yield).

Step 4: the Synthesis of 7-ethoxy-N$^4$-(3-ethynylphenyl)quinazoline-4,6-diamine (Compound 9)

7-ethoxy-N-(3-ethynylphenyl)-6-nitroquinazolin-4-amine (8 g, 0.024 mol) was dissolved in a mixture of 80 ml ethanol, 80 ml H$_2$O and 10 ml acetic acid. The reaction was heated to 70° C., then Fe (5.4 g, 0.096 mol) was added. The reaction mixture was heated to reflux for 4 hours. The resulting clear reaction solution was concentrated under reduced pressure to remove solvent. The pH of the residue was adjusted to 9 with 4N aqueous NaOH, and was washed with 200 ml EA/MeOH (50/1) until TLC show no product can be detected in the organic layer. The combined organic layers were concentrated, grey solid was precipitated and filtered to afford 7-ethoxy-N$^4$-(3-ethynylphenyl)quinazoline-4,6-diamine as grey solid 5.4 g (74.2% yield).

Step 5: the Synthesis of (E)-N-(7-ethoxy-4-((3-ethynylphenyl)amino)quinazolin-6-yl)-4-(piperidin-1-yl)but-2-enamide (Compound 11)

(E)-4-(piperidin-1-yl)but-2-enoic acid (550 mg, 3.4 mmol) and 10 drops of DMF were added in 20 ml DCM, and then oxalyl chloride (0.45 ml, 4.9 mmol) was added dropwise at 0° C. The solution was stirred for 1 hour at room temperature, then concentrated to a yellow solid. This intermediate was added in 50 ml THF, and then was added dropwisely into a solution of 7-ethoxy-N$^4$-(3-ethynylphenyl)quinazoline-4,6-diamine (1 g, 3.28 mmol) and DIPEA (1 g, 7.7 mmol) in 200 ml THF in a ice bath. The reaction was stirred at 40° C. for 4 hours. The resulting reaction solution was concentrated to remove the excess of solvent, the residue was separated between 20 ml DCM and 20 ml saturated aqueous NaHCO$_3$. The organic layer was concentrated and applied on a silica gel column (DCM/MeOH=10/1) to get (E)-N-(7-ethoxy-4-((3-ethynylphenyl)amino)quinazolin-6-yl)-4-(piperidin-1-yl)but-2-enamide as white solid 102 mg (6.8% yield). $^1$H-NMR (DMSO-d$^6$): δ1.41-1.53 (m, 9H), 2.36 (m, 4H), 3.10-3.12 (m, 2H), 4.17 (s, 1H), 4.26-4.33 (m, 2H), 6.55 (d, J=15.3 Hz, 1H), 6.76-6.83 (m, 1H), 7.19 (d, J=7.5 Hz, 1H), 7.26 (s, 1H), 7.35-7.40 (m, 1H), 7.88 (d, J=8.2 Hz, 1H), 8.00 (s, 1H), 8.52 (s, 1H), 8.92 (s, 1H), 9.49 (s, 1H), 9.71 (s, 1H). MS m/z 456 [M+1].

EXAMPLE 2

The Synthesis of (E)-N-(4-((3-ethynylphenyl)amino)-7-methoxyquinazolin-6-yl)-4-(piperidin-1-yl)but-2-enamide (Compound 12)

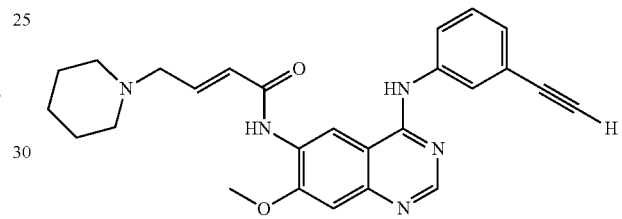

Compound 12 was prepared as an off-white solid using a similar procedure that described for the synthesis of compound 11. $^1$H-NMR (DMSO-d$^6$): δ1.40-1.41 (m, 2H), 1.52-1.53 (m, 4H), 2.36 (m, 4H), 3.10-3.12 (m, 2H), 4.01 (s, 3H), 4.17 (s, 1H), 6.56 (d, J=15.4 Hz, 1H), 6.75-6.84 (m, 1H), 7.19 (d, J=7.6 Hz, 1H), 7.28 (s, 1H), 7.35-7.41 (m, 1H), 7.88 (d, J=8.8 Hz, 1H), 8.00 (s, 1H), 8.53 s, 1H), 8.93 (s, 1H), 9.66 (s, 1H), 9.72 (s, 1H). MS m/z 442 [M+1].

EXAMPLE 3

The Synthesis of (E)-N-(4-((3-ethynylphenyl)amino)-7-(2-fluoroethoxy)quinazolin-6-yl)-4-(piperidin-1-yl)but-2-enamide (Compound 13)

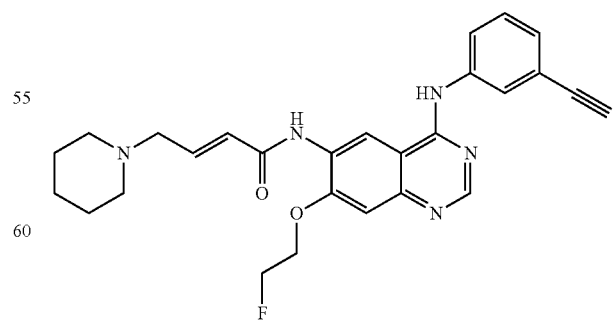

Compound 13 can be prepared as an off-white solid using a similar procedure that described for the synthesis of compound 11.

EXAMPLE 4

The Synthesis of (E)-N-(4-((3-ethynyl-4-fluorophenyl)amino)-7-methoxyquinazolin-6-yl)-4-(piperidin-1-yl)but-2-enamide (Compound 14)

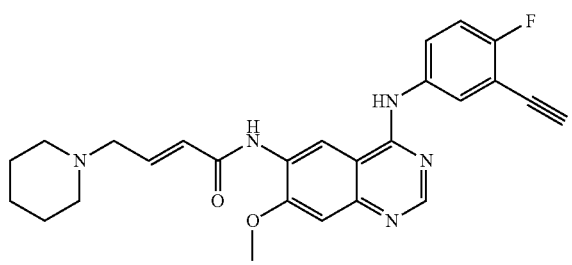 [SMILES: C#Cc1cc(Nc2ncnc3cc(OC)c(NC(=O)/C=C/CN4CCCCC4)cc23)ccc1F]

Compound 14 can be prepared as an off-white solid using a similar procedure that described for the synthesis of compound 11.

EXAMPLE 5

The Synthesis of (E)-N-(4-((3-ethynylphenyl)amino)-7-((tetrahydrofuran-3-yl)oxy)quinazolin-6-yl)-4-(piperidin-1-yl)but-2-enamide (Compound 15)

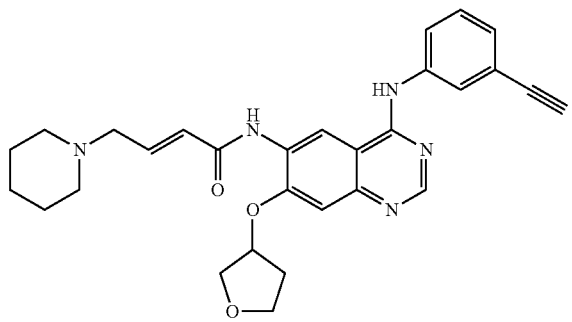 [SMILES: C#Cc1cccc(Nc2ncnc3cc(OC4CCOC4)c(NC(=O)/C=C/CN4CCCCC4)cc23)c1]

Compound 15 can be prepared as an off-white solid using a similar procedure that described for the synthesis of compound 11.

EXAMPLE 6

The Synthesis of (E)-N-(4-((3-ethynylphenyl)amino)-7-(2-methoxyethoxy)quinazolin-6-yl)-4-(piperidin-1-yl)but-2-enamide (Compound 16)

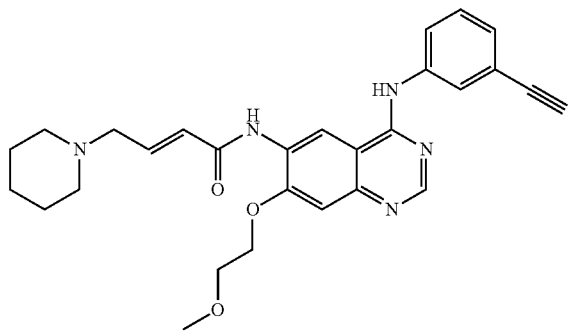 [SMILES: C#Cc1cccc(Nc2ncnc3cc(OCCOC)c(NC(=O)/C=C/CN4CCCCC4)cc23)c1]

Compound 16 can be prepared as an off-white solid using a similar procedure that described for the synthesis of compound 11.

EXAMPLE 7

The Synthesis of (E)-N-(4-((3-ethynylphenyl)amino)-7-$d_3$-methoxyquinazolin-6-yl)-4-(piperidin-1-yl)but-2-enamide (Compound 17)

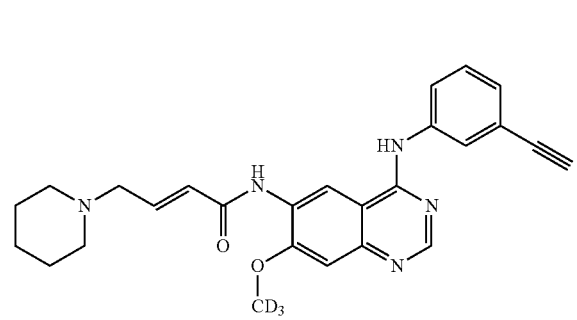 [SMILES: [2H]C([2H])([2H])Oc1cc2ncnc(Nc3cccc(C#C)c3)c2cc1NC(=O)/C=C/CN1CCCCC1]

Compound 17 can be prepared as an off-white solid using a similar procedure that described for the synthesis of compound 11.

EXAMPLE 8

The Synthesis of (E)-N-(7-$d_5$-ethoxy-4-((3-ethynylphenyl)amino)quinazolin-6-yl)-4-(piperidin-1-yl)but-2-enamide (Compound 18)

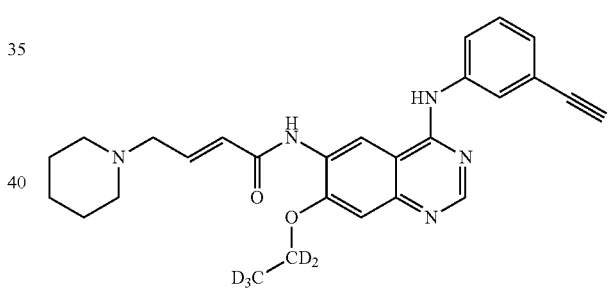

Compound 18 can be prepared as an off-white solid using a similar procedure that described for the synthesis of compound 11

The invention claimed is:

1. A compound of Formula I:

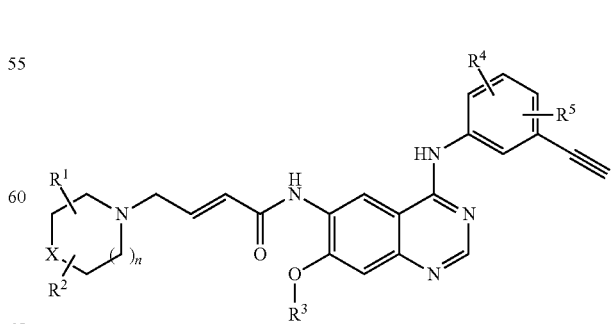

or a pharmaceutically acceptable salt, stereoisomer or tautomer thereof, wherein $R^1$ and $R^2$ are independently selected from hydrogen, $C_1$-$C_3$ alkyl, and F;

$R^3$ is selected from $C_1$-$C_6$ linear alkyl, $C_1$-$C_6$ branched alkyl, tetrahydrofuran-3-yl, —$(CH_2)_m$-morpholine, and —$(CH_2)_m$-piperazine-N($C_1$-$C_3$ alkyl), wherein $C_1$-$C_6$ linear alkyl and $C_1$-$C_6$ branched alkyl are optionally substituted by one or more halogens or $C_1$-$C_3$ alkoxy group;

m is 2 or 3;

n is 0, 2 or 3;

X is selected from carbon and N—$R^6$, with the proviso that when n is 0 or n is 3, X is neither O nor N—$R^6$;

$R^4$ and $R^5$ are independently selected from hydrogen, $C_1$-$C_3$ alkyl, F, and Cl;

$R^6$ is $C_1$-$C_3$ alkyl, optionally substituted by one or more halogens, hydroxy or $C_1$-$C_3$ alkoxy group.

2. The compound of claim 1, wherein said compound is according to Formula II:

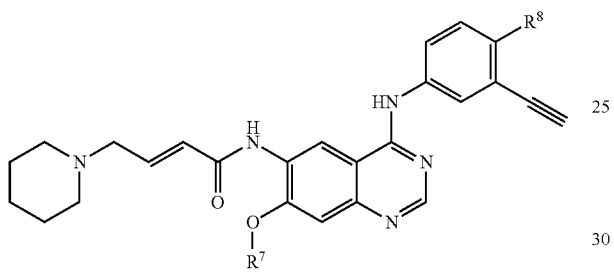

II or a pharmaceutically acceptable salt, stereoisomer or tautomer thereof, wherein $R^7$ is selected from $C_1$-$C_3$ linear alkyl, $C_1$-$C_3$ branched alkyl, and tetrahydrofuran-3-yl, wherein $C_1$-$C_3$ linear alkyl and $C_1$-$C_3$ branched alkyl are optionally substituted by one or more halogens or $C_1$-$C_3$ alkoxy group; and $R^8$ is H or F.

3. The compound of claim 2, wherein said compound is selected from the group consisting of:

(E)-N-(4-((3-ethynylphenyl)amino)-7-methoxyquinazolin-6-yl)-4-(piperidin-1-yl)but-2-enamide;

(E)-N-(7-ethoxy-4-((3-ethynylphenyl)amino)quinazolin-6-yl)-4-(piperidin-1-yl)but-2-enamide;

(E)-N-(4-((3-ethynylphenyl)amino)-7-(2-fluoroethoxy)quinazolin-6-yl)-4-(piperidin-1-yl)but-2-enamide;

(E)-N-(4-((3-ethynyl-4-fluorophenyl)amino)-7-methoxyquinazolin-6-yl)-4-(piperidin-1-yl)but-2-enamide;

(E)-N-(4-((3-ethynylphenyl)amino)-7-((tetrahydrofuran-3-yl)oxy)quinazolin-6-yl)-4-(piperidin-1-yl)but-2-enamide;

(E)-N-(4-((3-ethynylphenyl)amino)-7-(2-methoxyethoxy)quinazolin-6-yl)-4-(piperidin-1-yl)but-2-enamide;

(E)-N-(4-((3-ethynylphenyl)amino)-7-$d_3$-methoxyquinazolin-6-yl)-4-(piperidin-1-yl)but-2-enamide; and (E)-N-(7-$d_5$-ethoxy-4-((3-ethynylphenyl)amino)quinazolin-6-yl)-4-(piperidin-1-yl)but-2-enamide.

4. A pharmaceutical composition comprising a compound of claim 1 and a pharmaceutically acceptable carrier.

* * * * *